US012521239B2

(12) United States Patent
Morin et al.

(10) Patent No.: US 12,521,239 B2
(45) Date of Patent: Jan. 13, 2026

(54) LEAFLET/CUFF ATTACHMENT COMPLIANCE FOR IMPROVED DURABILITY

(71) Applicant: St. Jude Medical, Cardiology Division, Inc., St. Paul, MN (US)

(72) Inventors: Kristen T. Morin, St. Paul, MN (US); Jay Reimer, Shoreview, MN (US); Keith T. High, White Bear Lake, MN (US); Kristopher Henry Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 429 days.

(21) Appl. No.: 18/338,529

(22) Filed: Jun. 21, 2023

(65) Prior Publication Data

US 2023/0329862 A1 Oct. 19, 2023

Related U.S. Application Data

(63) Continuation of application No. 17/241,363, filed on Apr. 27, 2021, now Pat. No. 11,717,402.

(60) Provisional application No. 63/026,962, filed on May 19, 2020.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2427* (2013.01); *A61F 2220/0075* (2013.01)

(58) Field of Classification Search
CPC ........ A61F 2/24; A61F 2/2409; A61F 2/2412; A61F 2/2418; A61F 2/2427; A61F 2220/0075
See application file for complete search history.

(56) References Cited

U.S. PATENT DOCUMENTS

| | | | |
|---|---|---|---|
| 8,231,670 | B2 | 7/2012 | Salahieh |
| 9,962,260 | B2 | 5/2018 | Krans |
| 10,143,551 | B2 | 12/2018 | Braido |
| 10,441,421 | B2 | 10/2019 | Perszyk |
| 2012/0197390 | A1 | 8/2012 | Alkhatib |
| 2013/0150956 | A1 | 6/2013 | Yohanan |
| 2014/0005777 | A1 | 1/2014 | Anderl |
| 2014/0228945 | A1 | 8/2014 | Valdez |
| 2015/0073546 | A1 | 3/2015 | Braido |

(Continued)

OTHER PUBLICATIONS

European Search Report issued in Appln. No. 21174757.1 dated Oct. 28, 2021 (2 pages).

*Primary Examiner* — William H Matthews

(74) *Attorney, Agent, or Firm* — SLEMAN & LUND LLP

(57) ABSTRACT

A prosthetic heart valve may include an expandable stent having a plurality of struts forming cells connected to one another in a plurality of annular rows around the stent, a cuff attached to an annulus section of the stent by cuff sutures that have a plurality of stitches extending through material of the cuff and looping around the struts, and a plurality of leaflets each having a belly attached to the cuff within an interior region of the stent. The leaflets may together have a coapted position occluding the interior region of the stent and an open position in which the interior region is not occluded. The belly of each leaflet may be attached to the cuff by leaflet sutures extending in a path that crosses some of the struts in overlap zones. Those struts may be devoid of the stitches within the overlap zones.

20 Claims, 5 Drawing Sheets

(56) References Cited

U.S. PATENT DOCUMENTS

| | | | |
|---|---|---|---|
| 2015/0320556 | A1 | 11/2015 | Levi |
| 2018/0055631 | A1 | 3/2018 | Morin |
| 2021/0077254 | A1 | 3/2021 | Gale |

LEAFLET/CUFF ATTACHMENT COMPLIANCE FOR IMPROVED DURABILITY

CROSS-REFERENCE TO RELATED APPLICATIONS

This application is a continuation of U.S. application Ser. No. 17/241,363 filed Apr. 27, 2021, which claims the benefit of the filing date of U.S. Provisional Patent Application No. 63/026,962 filed May 19, 2020, the disclosures of which are hereby incorporated herein by reference.

BACKGROUND OF THE INVENTION

The present disclosure relates in general to heart valve replacement and, in particular, to prosthetic heart valves. More particularly, the present disclosure relates to leaflets for use in prosthetic heart valves.

Open-heart and transcatheter heart valve replacements are increasingly being performed in lower-risk patients. Such patients are typically younger than the higher-risk patient population that has traditionally received prosthetic heart valves, so they have a longer remaining life expectancy than traditional prosthetic heart valve recipients.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to collapsible prosthetic heart valves, conventional prosthetic heart valves suffer from some shortcomings. For example, in conventional collapsible prosthetic heart valves, the leaflets are typically made from biological tissue, such as porcine tissue. Over an extended patient lifespan, such biological leaflets may eventually erode or tear, creating a need for further surgical intervention or an additional valve replacement.

Biological leaflets may fail when excessively loaded or abraded. Biological leaflets have decent durability but may wear on the edges where they attach to the frame. Stresses in the tissue leaflets may limit valve durability by causing functional failures through tears or hole formation or acting as nodes for calcification initiation. There therefore is a need for further improvements to collapsible prosthetic heart valves. Among other advantages, the present invention may address one or more of these needs.

BRIEF SUMMARY OF THE INVENTION

The disclosure herein describes multiple embodiments of a prosthetic heart valve that include an expandable stent having an inflow end, an outflow end, an annulus section adjacent the inflow end, and a plurality of struts forming cells connected to one another in a plurality of annular rows around the stent; a cuff attached to the annulus section of the stent by cuff sutures that have a plurality of stitches extending through material of the cuff and looping around the struts; and a plurality of leaflets each having a belly attached to the cuff within an interior region of the stent, the leaflets together having a coapted position occluding the interior region of the stent and an open position in which the interior region is not occluded, the belly of each leaflet being attached to the cuff by leaflet sutures extending in a path that crosses some of the struts in overlap zones, wherein the some of the struts are devoid of the stitches within the overlap zones, such that movement of the leaflets causes the cuff to pull away from the stent at locations within the overlap zones in a radially inward direction perpendicular to a flow direction through the prosthetic heart valve.

Also described herein are multiple embodiments of a prosthetic heart valve that include an expandable stent having an inflow end, an outflow end, an annulus section adjacent the inflow end, a plurality of struts forming cells connected to one another in a plurality of annular rows around the stent, a plurality of junctions at locations at which adjacent ones of the struts join one another, and a plurality of cantilevered portions each extending away from at least one of the struts; a cuff attached to the annulus section of the stent by cuff sutures that have a plurality of stitches extending through material of the cuff and looping around the struts and the cantilevered portions; and a plurality of leaflets each having a belly attached to the cuff within an interior region of the stent, the leaflets together having a coapted position occluding the interior region of the stent and an open position in which the interior region is not occluded, the belly of each leaflet being attached to the cuff by leaflet sutures extending in a path that crosses some of the cantilevered portions in overlap zones, wherein movement of the leaflets causes the cantilevered portions to bend in a radially inward direction at locations within the overlap zones, the radially inward direction being perpendicular to a flow direction through the prosthetic heart valve.

Further described herein are multiple embodiments of a method of flowing a fluid through a prosthetic heart valve having a plurality of leaflets. The method includes moving the leaflets between an open position and a coapted position, the leaflets being coupled to an expandable stent having a plurality of struts forming cells connected to one another in a plurality of annular rows around the stent, the leaflets each having a belly attached to a cuff disposed within an interior region of the stent, the cuff being attached to the annulus section of the stent by cuff sutures that have a plurality of stitches extending through material of the cuff and looping around the struts, the belly of each leaflet being attached to the cuff by leaflet sutures extending in a path that crosses selected ones of the struts in overlap zones, the leaflets in the coapted position occluding the interior region of the stent, and the leaflets in the open position not occluding the interior region, wherein movement of the leaflets causes the cuff to move in a radially inward direction at locations within the overlap zones, the radially inward direction being perpendicular to a flow direction of the fluid through the interior region of the stent, the movement of the cuff in the radially inward direction resulting from either (1) the selected ones of the struts being devoid of the stitches within the overlap zones, or (2) the stent including cantilevered portions in the overlap zones such that movement of the cuff in the radially inward direction causes the cantilevered portions of the stent to bend in the radially inward direction.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein in connection with a prosthetic heart valve, the term "inflow end" refers to the end of the heart valve through which blood enters when the heart valve is functioning as intended, and the term "outflow end" refers to the end of the heart valve through which blood exits when the heart valve is functioning as intended. As used herein in connection with a prosthetic heart valve, the term "proximal" refers to the inflow end of the prosthetic heart valve or to elements of the heart valve that are relatively close to the inflow end, and the term "distal" refers to the outflow end of the heart valve or to elements of the heart valve that are relatively close to the outflow end. Also as used herein, the terms "generally," "substantially," "approximately," and "about" are intended to mean that slight deviations from absolute are included within the scope of the term so modified.

When used to indicate relative locations within the prosthetic heart valve, the terms "longitudinal" and "vertical" are to be taken as the direction of the axis extending between the inflow end and the outflow end of the stent of the heart valve, along the direction of intended blood flow; the term "flow direction" is to be taken as the direction from the inflow end to the outflow end of the stent of the heart valve; and the terms "above," "below," "high," and "low" are to be taken as relative to the inflow end of the stent. "Above" and "high" are to be understood as relatively farther from the inflow end of the stent in the direction of intended blood flow, and "below" and "low" are to be understood as relatively closer to the inflow end of the stent in the direction of intended blood flow. When used to indicate relative locations within the prosthetic heart valve, the term "circumferential" is to be taken as the direction of rotation about the longitudinal axis of the stent.

Figure 1:
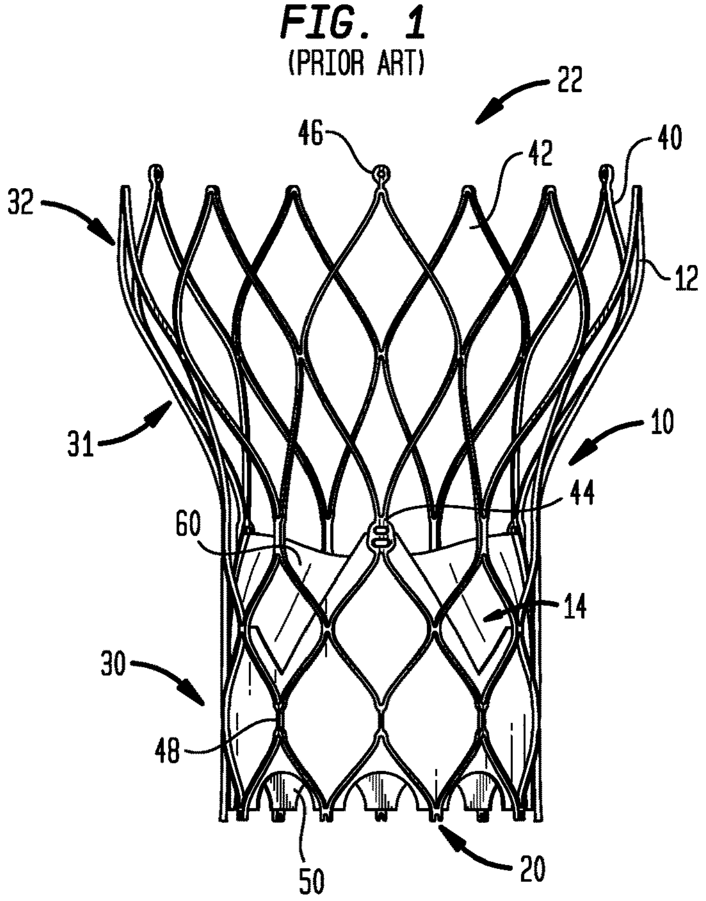
FIG. 1 (PRIOR ART)
FIG. 1 is a side view of a conventional expandable and/or collapsible prosthetic heart valve.
Figure 2:
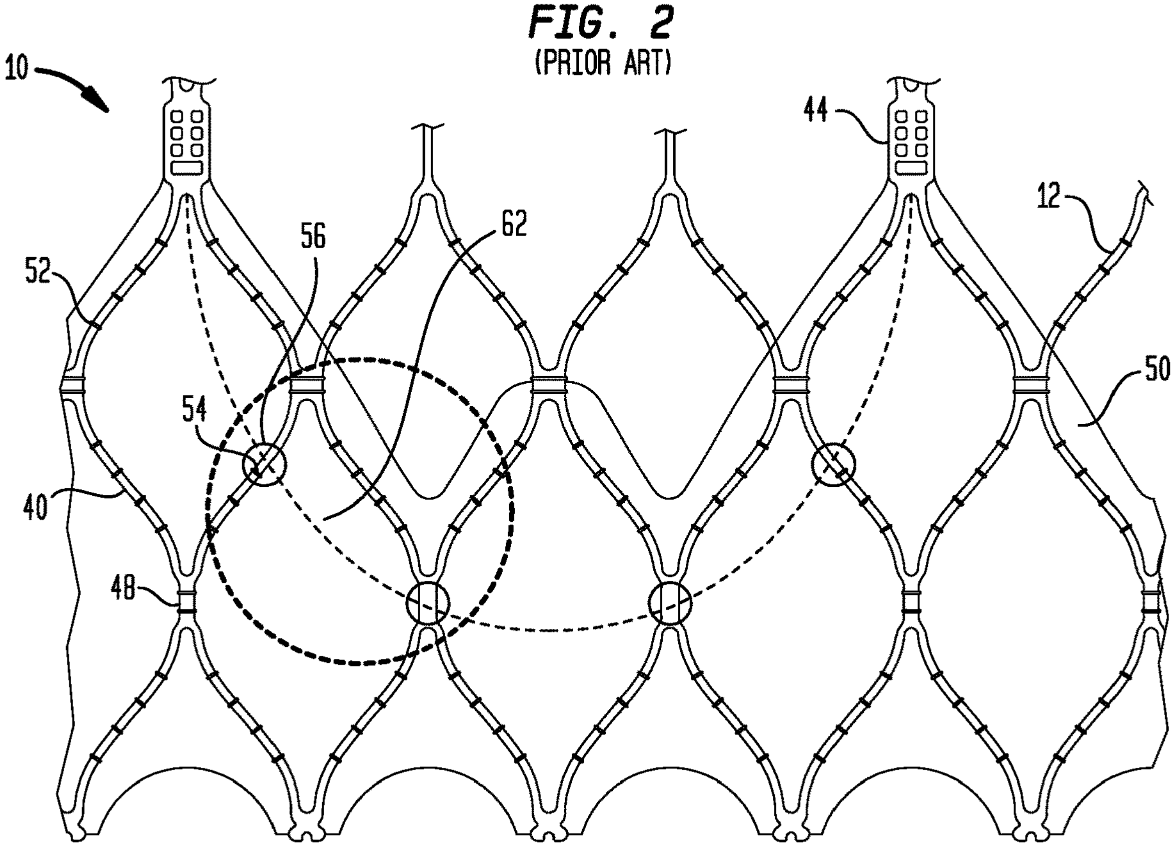
FIG. 2 (PRIOR ART)
FIG. 2 is a side view of a portion of the prosthetic heart valve of FIG. 1.

FIGS. 1 and 2 illustrate a collapsible and/or expandable stent-supported prosthetic heart valve 10 including a stent 12 and a valve assembly 14 as is known in the art. The prosthetic heart valve 10 is designed to replace a native heart valve of a patient, such as a native aortic valve, mitral valve, pulmonary valve, or tricuspid valve. It should be noted that while the example of FIG. 1 is described as a prosthetic aortic valve having a stent with a shape as illustrated, the valve could be a bicuspid valve, such as the mitral valve, and the stent could have different shapes, such as a flared or conical annulus section, a less-bulbous aortic section, and the like, and a differently shaped transition section between the annulus section and the aortic section. Any details of the structure and function of the prosthetic heart valve 10 that are not described herein may be found in U.S. Pat. No. 10,143,551, the entire disclosure of which is hereby incorporated by reference herein.

The stent 12 may be formed from biocompatible materials that are capable of self-expansion or expansion via a balloon, including, for example, shape-memory alloys such as nitinol, or other suitable metals or polymers. The stent 12 extends from an inflow or annulus end 20 to an outflow or aortic end 22 and includes an annulus section 30 adjacent the inflow end, a transition section 31, and an aortic section 32 adjacent the outflow end. Each of the sections of stent 12 includes a plurality of struts 40 forming cells 42 connected to one another in one or more annular rows around the stent. For example, as shown in FIG. 1, the annulus section 30 may have two annular rows of complete cells 42 and the aortic section 32 and the transition section 31 may each have one or more annular rows of partial cells. The stent 12 may include a plurality of junctions 48 at locations at which adjacent struts 40 connect to one another. The stent 12 may also include one or more retaining elements 46 at the outflow end 22 (or, depending on the delivery path, at the inflow end 20), the retaining elements being sized and shaped to cooperate with female retaining structures (not shown) provided within a transcatheter delivery device.

The prosthetic heart valve 10 includes the valve assembly 14, preferably positioned in the annulus section 30 of the stent 12 and secured to the stent. The valve assembly 14 includes a cuff 50 and a plurality of leaflets 60 that collectively function as a one-way valve by coapting with one another. As a prosthetic aortic valve, the prosthetic heart valve 10 has three leaflets 60. However, it will be appreciated that other prosthetic heart valves with which the leaflets of the present disclosure may be used may have a greater or lesser number of leaflets. Both the cuff 50 and the leaflets 60 may be wholly or partly formed of any suitable biological material (e.g., animal tissue such as pericardium tissue), fabric, or polymer that is impermeable to liquid such as, for example, polytetrafluoroethylene (PTFE), polyvinyl alcohol (PVA), ultra-high molecular weight polyethylene (UHMWPE), silicone, urethane, and the like. The cuff 50 and the leaflets 60 may be formed of the above materials or any of the additional materials described in U.S. provisional patent application 62/902,044, the disclosure of which is hereby incorporated by reference herein.

As can be seen in FIG. 1, commissure attachment features 44 may lie at the intersection of four cells 42, two of the cells being adjacent one another in the same annular row, and the other two cells being in different annular rows and lying in end-to-end relationship. Each of the commissure attachment features 44 may include one or more eyelets that facilitate the suturing of leaflet commissures to the stent 12.

The leaflets 60 are configured to move between the open position shown in FIG. 1 and a closed position in which the leaflets occlude a central opening of the valve assembly 14. The leaflets 60 are configured such that they are in the open position when the blood pressure at the annulus end 20 of the stent 12 is greater than the blood pressure at the aortic end 22 and are in the closed position when the blood pressure at the aortic end is greater than the blood pressure at the annulus end.

Referring to FIG. 2, the cuff 50 may be attached to the stent 12 by cuff sutures 52 that extend through material of the cuff and loop around the struts 40 in a series of cuff stitches 54. The leaflets 60 may be attached along their belly portions to the cuff 50 by leaflet sutures 62, and the commissure between adjacent leaflets may be attached to commissure attachment features 44 of the stent 12. Some of the stitches 54 loop around the struts 40 in overlap zones 56 that are adjacent to locations at which the leaflet sutures 62 cross one of the struts.

As used herein, an "overlap zone" is a location at which an edge of a belly portion of one of the leaflets 60 is positioned adjacent to a strut 40 of the stent 12, such that in a side view (e.g., the side view shown in FIG. 2), the edge of the belly portion of the leaflet appears to "overlap" one of the struts. It is within these "overlap zones" that the belly portion of the leaflets 60 may experience the maximum stress in an embodiment such as the prosthetic heart valve 10 of FIG. 2, since the belly portion is sutured to the cuff 50 at a location where the cuff cannot flex much, since the cuff is sutured to the stent 12 at the same locations.

The prosthetic heart valve 10 may be used to replace a native aortic valve, a surgical heart valve, a heart valve that has undergone a surgical procedure, or any other valve that it is desired to replace. The prosthetic heart valve 10 may be delivered to the desired site (e.g., near or proximate a native valve annulus, or near or proximate an annuloplasty ring or other repair device) using any suitable delivery device.

During delivery, the prosthetic heart valve 10 may be disposed inside a transcatheter delivery device in a collapsed condition. The delivery device may be introduced into a patient using a transfemoral, transapical, transseptal, transradial, transsubclavian, transaortic or any other percutaneous approach. Once the delivery device has reached the target site, the user may deploy the prosthetic heart valve 10. Upon deployment, the prosthetic heart valve 10 expands so that the annulus section 30 is in secure engagement within the native valve annulus (or in engagement with an annuloplasty ring or other repair device). When the prosthetic heart valve 10 is properly positioned, it works as a one-way valve, allowing blood to flow in the flow direction, and preventing blood from flowing in the opposite direction.

Finite element analysis (FEA) indicates the highest stress zones (predicted areas for durability failure of the leaflets 60) are near points of leaflet attachment in the overlap zones 56 that are near the struts 40 of the stent 12. The amount of compliance or "give" at the suture attachment points between the cuff 50 and the leaflets 60 (i.e., the "cuff attachment points") is likely to increase the further the cuff attachment points are from one of the struts 40, as the struts have a significantly higher modulus of elasticity (stiffer) in comparison to the cuff material. The compliance at cuff attachment points in the overlap zones 56 near the struts 40 is primarily influenced by the stiffness of the strut, whereas the compliance at cuff attachment points outside of the overlap zones will be more influenced by the cuff material.

The leaflets 60 bear stress when loaded during both opening and coaptation. The embodiments that will be described below with reference to FIGS. 3A through 5B may redistribute the load borne by the leaflets when the leaflets move back and forth between an open position and a coapted position.

Figure 3A:
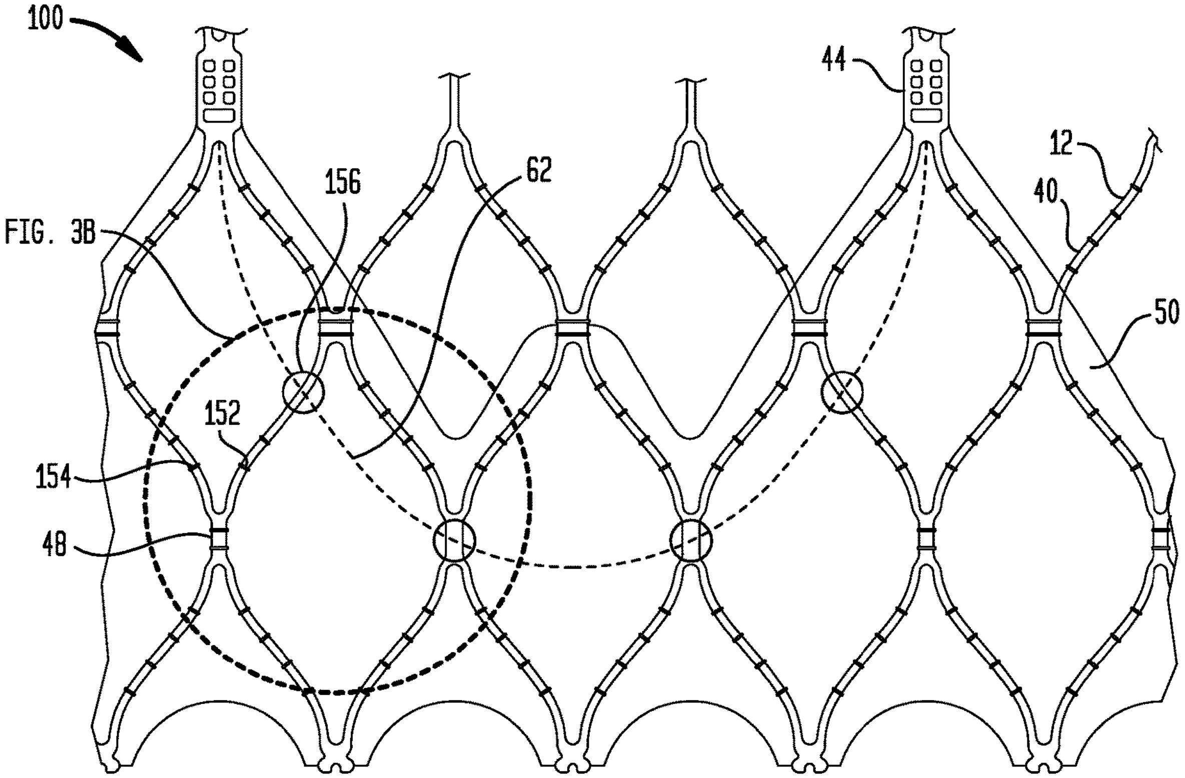
FIG. 3A is a side view of a portion of a prosthetic heart valve according to an embodiment of the present invention.
Figure 3B:
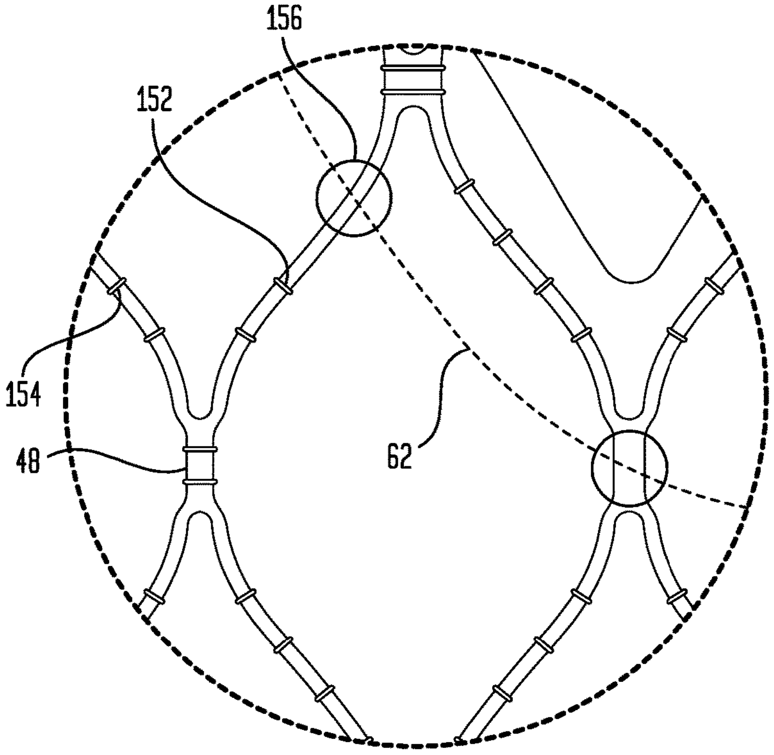
FIG. 3B is an enlarged side view of an overlap zone of the prosthetic heart valve of FIG. 3A.

FIGS. 3A and 3B illustrate a portion of a prosthetic heart valve 100 that is a variant of the prosthetic heart valve 10 described above. The prosthetic heart valve 100 is the same as the prosthetic heart valve 10, except that the prosthetic heart valve 100 has a different pattern of sutures 152 that attaches the cuff 50 to the stent 12. It can be most clearly seen in FIG. 3B that the stitches 154 of the cuff sutures 152 have been removed from the overlap zones 156 near the struts 40, such that the cuff 50 is attached to the stent 12 only at locations outside of the overlap zones. In this embodiment, by removing the sutures 152 within the overlap zones, the stress on the leaflets 60 within the locations of maximum stress of the embodiment of FIG. 2 can be redistributed, such that the edge of the belly of each the leaflets is only attached to the cuff 50 at locations where the cuff can pull away from the stent 12 to redistribute the stress over a greater portion of the belly of the leaflets, instead of having the stress more concentrated within the overlap zones.

Although the leaflets 60 are attached to the cuff 50 by the leaflet sutures 62 both inside and outside the overlap zones 156, the elimination of the cuff stitches 154 within the overlap zones may increase the compliance at the cuff attachment points by permitting the cuff to pull away from the stent 12 at the overlap zones when the leaflets are moving, thereby reducing the stress concentration on the leaflets at the cuff attachment points within the overlap zones. As a consequence of the elimination of the stitches 154 within the overlap zones 156, the stress experienced by the leaflets 60 during opening and coaptation of the leaflets may be redistributed to be more evenly spread out across the belly of the leaflets, thereby improving the durability of the leaflets.

To eliminate the cuff stitches 154 within each of the overlap zones 156 without having to use multiple lengths of suture 152 in each zone, the suture may extend across the overlap zone without extending through the material of the cuff 50. Alternatively, the cuff suture 152 may be looped around the struts 40 within the overlap zone 156 without extending through the material of the cuff 50. In one example, two to four cuff stitches 154 may be eliminated from each of the overlap zones 156, such that up to half of the length of a strut 40 extending between two adjacent junctures 48 may be devoid of stitches.

Figure 4:
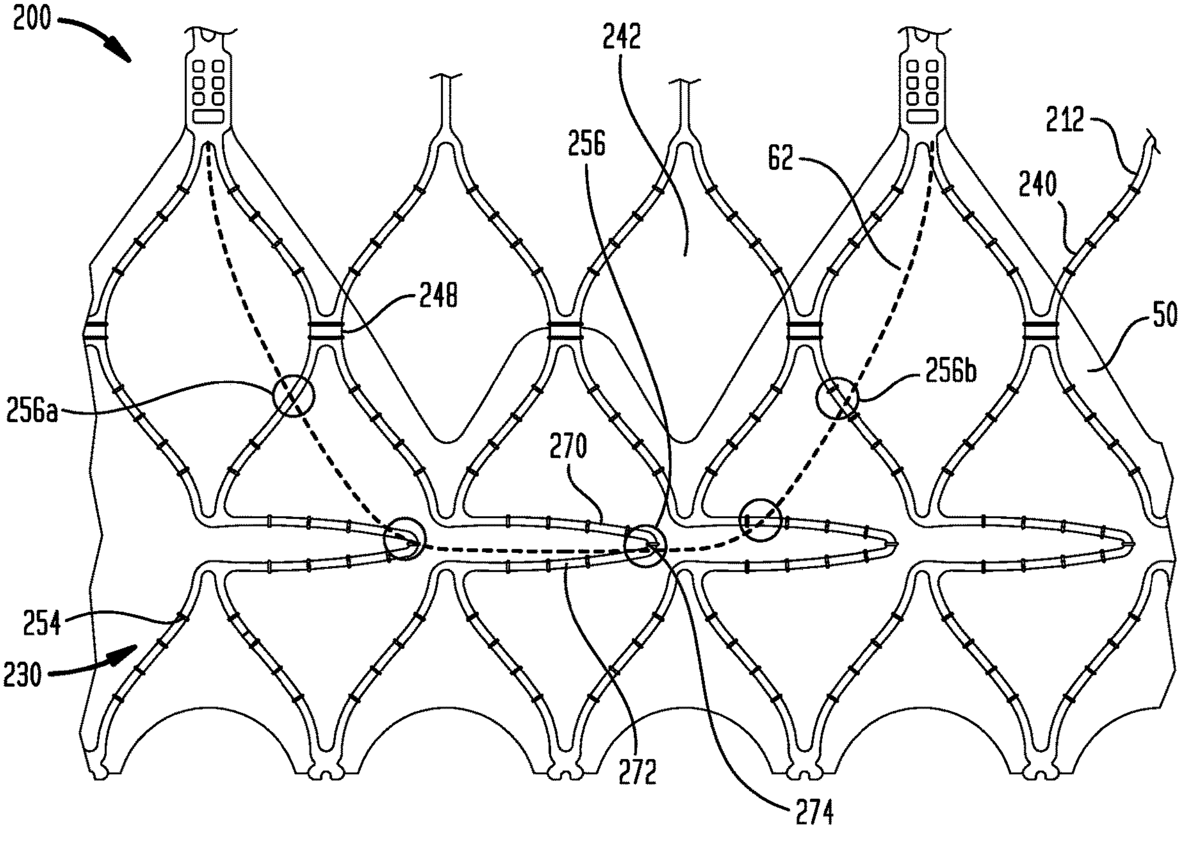
FIG. 4 is a side view of a portion of a prosthetic heart valve according to another embodiment of the present invention.

FIG. 4 illustrates a portion of a prosthetic heart valve 200 that is another variant of the prosthetic heart valve 10 described above. The prosthetic heart valve 200 is the same as the prosthetic heart valve 10, except that the stent 212 of the prosthetic heart valve 200 has cantilevered portions 270 that replace the junctions 248 between adjacent cells 242 within the first row of complete cells in the annulus section 230. The cantilevered portions 270 have two arms 272 that extend in a circumferential direction generally perpendicular to the flow direction of the valve and that are joined to one another at a joint 274.

At the locations of the cantilevered portions 270, the stent 212 may be radially weaker, that is, less resistant to radial forces because the cantilevered portions may move radially inward and outward in response to forces applied from the leaflets 60. In this variant, the cuff stitches 254 may not be eliminated from the overlap zones 256 (i.e., locations adjacent to where the leaflet sutures 62 cross a cantilevered portion) near the cantilevered portions 270. Nonetheless, when the leaflets 60 are loaded during opening and coaptation of the leaflets, there may be less localized stress applied to the leaflets at the overlap zones 256 due to the increased compliance of the stent 212 and cuff 50 at the cantilevered portions 270.

The prosthetic heart valve 200 may also have second overlap zones 256*a* and 256*b*, at which the leaflet sutures 62 overlap with locations of the struts 240. The cuff stitches 254 may be eliminated from some of the second overlap zones 256*a* and may not be eliminated from other of the second overlap zones 256*b*. The inclusion of some second overlap zones 256*a* that are devoid of cuff stitches 254 may reduce the stress concentration on the leaflets at the cuff attachment points within the second overlap zones in addition to the reduction of stress concentration at the cuff attachment points within the overlap zones 256.

Although the leaflets 60 are attached to the cuff 50 by the sutures 62 both within and outside the overlap zones 256, the replacement of the junctions 248 with the cantilevered portions 270 within the overlap zones may increase the compliance at the cuff attachment points by permitting the stent 212 to flex radially inward at the overlap zones when the leaflets are moving, thereby reducing the stress concentration on the leaflets at the cuff attachment points within the overlap zones. As a consequence, the stress experienced by the leaflets 60 during opening and coaptation of the leaflets may be redistributed to be more evenly spread out across the belly of the leaflets, thereby improving the durability of the leaflets.

In other examples, the cantilevered portions 270 may be varied in length in the circumferential direction, and the width of the arms 272 may be varied. The shape of the cantilevered portions 270 may also be varied, such that the arms 272 may have a non-linear shape (e.g., curved, undulating, etc.) In some examples, only some of the junctions 248 between adjacent cells 242 in the first row of cells may be replaced with cantilevered portions. Although FIG. 4 shows some of the cuff stitches 254 extending around the cantilevered portions 270, that need not always be the case. In some variants, as will be described below with respect to FIGS. 5A and 5B, the size or shape of the cantilevered portions may be designed such that the path of the leaflet sutures 62 connecting the leaflets 60 to the cuff 50 has minimal or no overlap with the cantilevered portions. In some examples, enough cantilevered portions 270 may be provided that the path of the leaflet sutures 62 overlaps with the stent 212 only at the cantilevered portions. In some variants, the cantilevered portions 270 may extend upward parallel to the flow direction from some of the junctions 248 and/or downward parallel to the flow direction from some of the junctions.

Figure 5A:
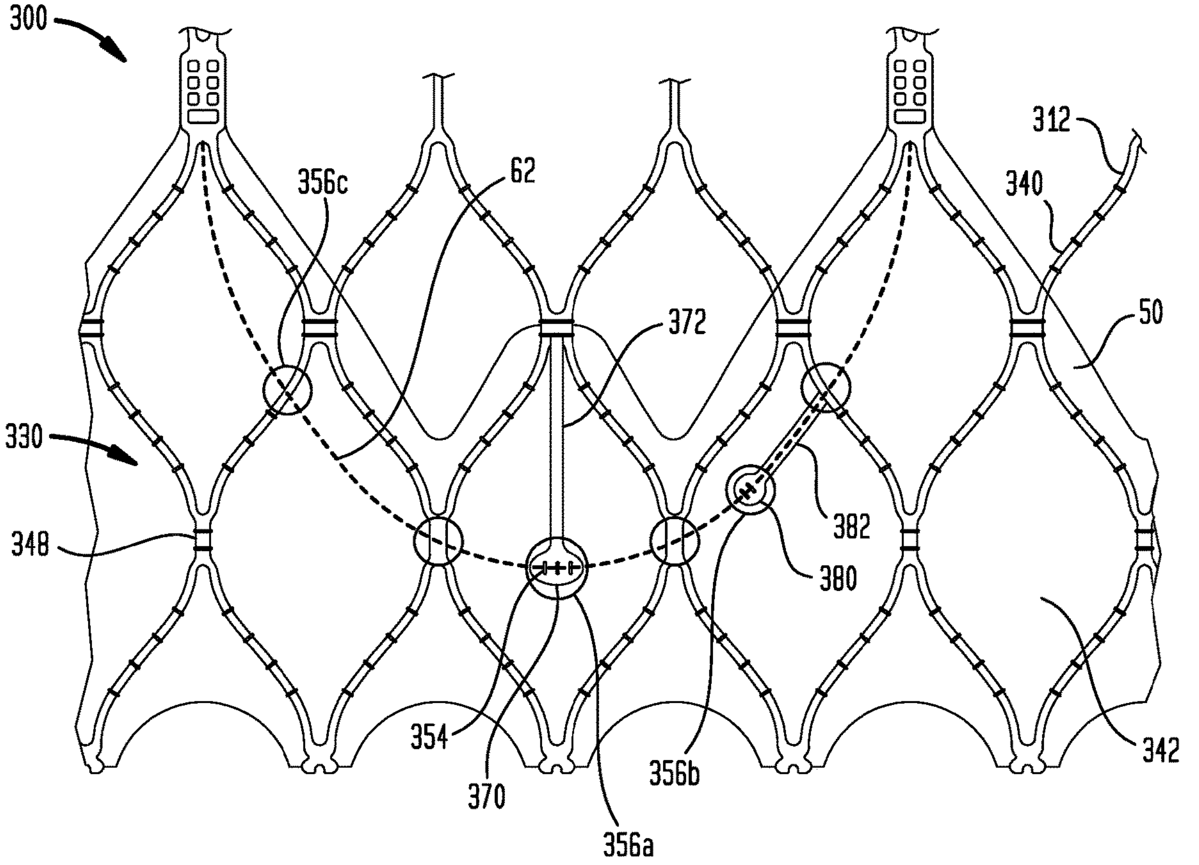
FIG. 5A is a side view of a portion of a prosthetic heart valve according to another embodiment of the present invention.

FIG. 5A illustrates a portion of a prosthetic heart valve 300 that is a variant of the prosthetic heart valve 100 described above. The prosthetic heart valve 300 is the same as the prosthetic heart valve 100, except that the stent 312 of the prosthetic heart valve 300 has cantilevered portions 370 and 380 that extend from the junctions 348 between adjacent cells 342 within the first or second row of complete cells in the annulus section 330. The cantilevered portion 370 has an arm 372 that extends downward parallel to the flow direction from one of the junctions 348. The cantilevered portion 380 has an arm 382 that extends in a diagonal direction that is transverse to the flow direction of the valve. In other variations (not shown), the cantilevered portions may have an arm that extends in a circumferential direction generally perpendicular to the flow direction of the valve.

Similar to the cantilevered portions 270, at the locations of the cantilevered portions 370 and 380, the stent 312 may be radially weaker, that is, less resistant to radial forces because the cantilevered portions may move radially inward and outward in response to forces applied from the leaflets 60. In this variant, the cuff stitches 354 may not be eliminated from the overlap zones 356*a*, 356*b* where the leaflet sutures 62 cross the respective cantilevered portions 370, 380, but the cuff stitches preferably are eliminated from the overlap zones 356*c* at which the leaflet sutures 62 cross the struts 340. Nonetheless, compared to the embodiment of FIGS. 1 and 2, when the leaflets 60 are loaded during opening and coaptation of the leaflets, there may be less localized stress applied to the leaflets at the overlap zones 356*a*, 356*b* due to the increased compliance of the stent 312 and cuff 50 at the cantilevered portions 370, 380.

The prosthetic heart valve 300 may also have second overlap zones 356*c*, at which the leaflet sutures 62 overlap with locations of the struts 340. The cuff stitches 354 may be eliminated from some or all of the second overlap zones 356*c*. The inclusion of some second overlap zones 356*c* that are devoid of stitches 354 may reduce the stress concentration on the leaflets at the cuff attachment points within the second overlap zones in addition to the reduction of stress concentration at the cuff attachment points within the overlap zones 356*a* and 356*b*.

Although the leaflets 60 are attached to the cuff 50 by the leaflet sutures 62 both within and outside the overlap zones 356*a*, 356*b*, the addition of the cantilevered portions 370, 380 within the overlap zones, combined with the elimination of the cuff stitches 354 from the second overlap zones 356*c*, may increase the compliance at the cuff attachment points compared to the embodiment of FIGS. 1 and 2 by permitting the stent 312 to flex radially inward at the overlap zones 356*a*, 356*b*, and 356*c* when the leaflets are moving. As a consequence, the stress experienced by the leaflets 60 during opening and coaptation of the leaflets may be more evenly spread out across the belly of the leaflets, thereby improving the durability of the leaflets. In another variant, the embodiment of FIG. 5A may be modified by removing one or more of the junctions 348 to further increase the compliance of the stent at the cuff attachment points compared to the embodiment of FIG. 5A. Such a variation may require some replacement structure such as replacing the junctions 348 with a suture to join the portions of the stent 312 that are adjacent to the locations at which the junctions are removed.

Figure 5B:
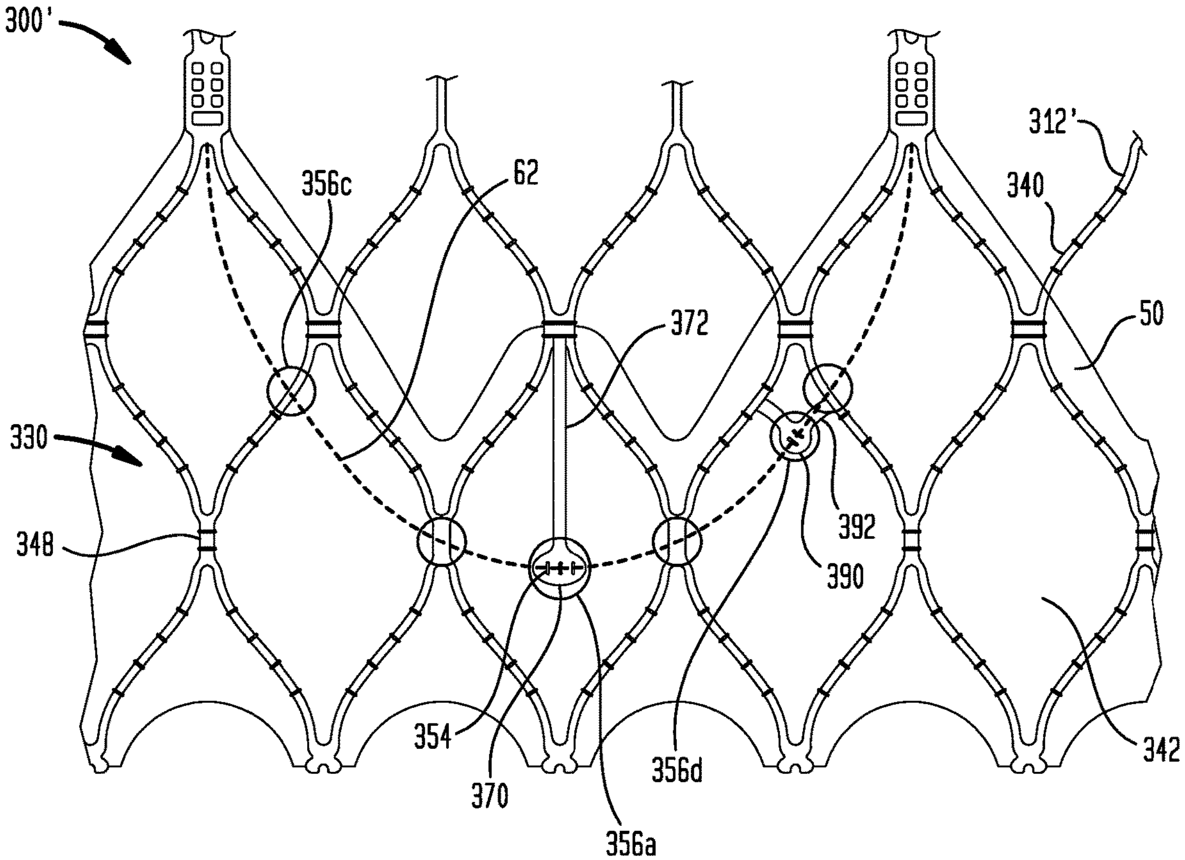
FIG. 5B is a side view of a portion of a prosthetic heart valve according to another embodiment of the present invention.

In a further example, FIG. 5B illustrates a portion of a prosthetic heart valve 300' that is a variant of the prosthetic heart valve 300 described above. The prosthetic heart valve 300' is the same as the prosthetic heart valve 300, except that the stent 312' of the prosthetic heart valve 300' has a cantilevered portion 390 that extends from adjacent struts 340 of a single cell 342 within the first or second row of complete cells in the annulus section 330. The cantilevered portion 390 has two arms 392 that extend from adjacent struts 340 diagonally downward in directions transverse to the flow direction of the valve to connect with one another. In this variant, the cuff stitches 354 may not be eliminated from the overlap zones 356*a*, 356*d* where the leaflet sutures 62 cross the respective cantilevered portions 370, 390, but the cuff stitches preferably are eliminated from the overlap zones 356*c* at which the leaflet sutures 62 cross the struts 340. As with the embodiment of FIG. 5A, when the leaflets 60 are loaded during opening and coaptation of the leaflets, there may be less localized stress applied to the leaflets at the overlap zones 356*a*, 356*d* due to the increased compliance of the stent 312 and cuff 50 at the cantilevered portions 370, 390.

Although the embodiments of FIGS. 3A-5B have been described separately above, aspects of any two or all three embodiments may be combined into a single prosthetic heart valve. For example, different types of cantilevered portions may be combined in a single embodiment, and some of the overlap zones may be devoid of cuff stitches, while other overlap zones may include cuff stitches.

In summary, the disclosure herein describes multiple embodiments of a prosthetic heart valve that includes an expandable stent having an inflow end, an outflow end, an annulus section adjacent the inflow end, and a plurality of struts forming cells connected to one another in a plurality of annular rows around the stent; a cuff attached to the annulus section of the stent by cuff sutures that have a plurality of stitches extending through material of the cuff and looping around the struts; and a plurality of leaflets each having a belly attached to the cuff within an interior region of the stent, the leaflets together having a coapted position occluding the interior region of the stent and an open position in which the interior region is not occluded, the belly of each leaflet being attached to the cuff by leaflet sutures extending in a path that crosses some of the struts in overlap zones, wherein the some of the struts are devoid of the stitches within the overlap zones, such that movement of the leaflets causes the cuff to pull away from the stent at locations within the overlap zones in a radially inward direction perpendicular to a flow direction through the prosthetic heart valve; and/or the cuff may be attached to the stent only at locations outside of the overlap zones; and/or the cuff sutures may extend across the overlap zones without extending through the material of the cuff; and/or the cuff sutures may be looped around the struts within the overlap zones without extending through the material of the cuff.

Also described herein are multiple embodiments of a prosthetic heart valve that includes an expandable stent having an inflow end, an outflow end, an annulus section adjacent the inflow end, a plurality of struts forming cells connected to one another in a plurality of annular rows around the stent, a plurality of junctions at locations at which adjacent ones of the cells join one another, and a plurality of cantilevered portions each extending away from at least one of the struts; a cuff attached to the annulus section of the stent by cuff sutures that have a plurality of stitches extending through material of the cuff and looping around the struts and the cantilevered portion; and a plurality of leaflets each having a belly attached to the cuff within an interior region of the stent, the leaflets together having a coapted position occluding the interior region of the stent and an open position in which the interior region is not occluded, the belly of each leaflet being attached to the cuff by leaflet sutures extending in a path that crosses some of the cantilevered portions in overlap zones, wherein movement of the leaflets causes the cantilevered portions to bend in a radially inward direction at locations within the overlap zones, the radially inward direction being perpendicular to a flow direction through the prosthetic heart valve; and/or each of the cantilevered portions may extend in a circumferential direction generally perpendicular to the flow direction; and/or each of the cantilevered portions may include two arms that extend in the circumferential direction and that are joined to one another at a joint; and/or each arm of each of the cantilevered portions may be joined to and may extend away from a corresponding one of the struts; and/or each of the cantilevered portions may be spaced apart from the inflow end of the stent by a same distance; and/or at least one of the cantilevered portions may extend generally parallel to the flow direction; and/or the overlap zones may be first overlap zones, some of the leaflet sutures may cross some of the struts in second overlap zones, and the some of the struts may be devoid of the stitches within the second overlap zones.

Further described herein are multiple embodiments of a method of flowing a fluid through a prosthetic heart valve having a plurality of leaflets. The method includes moving the leaflets between an open position and a coapted position, the leaflets being coupled to an expandable stent having a plurality of struts forming cells connected to one another in a plurality of annular rows around the stent, the leaflets each having a belly attached to a cuff disposed within an interior region of the stent, the cuff being attached to the annulus section of the stent by cuff sutures that have a plurality of stitches extending through material of the cuff and looping around the struts, the belly of each leaflet being attached to the cuff by leaflet sutures extending in a path that crosses selected ones of the struts in overlap zones, the leaflets in the coapted position occluding the interior region of the stent, and the leaflets in the open position not occluding the interior region, wherein movement of the leaflets causes the cuff to move in a radially inward direction at locations within the overlap zones, the radially inward direction being perpendicular to a flow direction of the fluid through the interior region of the stent, the movement of the cuff in the radially inward direction resulting from either (1) the selected ones of the struts being devoid of the stitches within the overlap zones, or (2) the stent including cantilevered portions in the overlap zones such that movement of the cuff in the radially inward direction causes the cantilevered portions of the stent to bend in the radially inward direction; and/or selected ones of the struts may be devoid of the stitches within the overlap zones; and/or when the cuff is pulled in the radially inward direction at the locations within the overlap zones, the cuff may pull away from the stent at the locations within the overlap zones; and/or the cuff sutures may extend across the overlap zones without extending through the material of the cuff; and/or the cuff sutures may be looped around the struts within the overlap zones without extending through the material of the cuff; and/or wherein the stent may include cantilevered portions in the overlap zones such that movement of the cuff in the radially inward direction causes the cantilevered portions of the stent to bend in the radially inward direction; and/or each of the cantilevered portions may extend in a circumferential direction generally perpendicular to the flow direction; and/or each of the cantilevered portions may include a plurality of arms that are joined to and that extend away from a corresponding one of the struts; and/or at least one of the cantilevered portions may extend generally parallel to the flow direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:

an expandable stent having an inflow end, an outflow end, an annulus section adjacent the inflow end, a plurality of struts forming cells connected to one another in a plurality of annular rows around the stent, the cells in each of the annular rows being connected to adjacent cells in a same annular row at junctions, at least some of the junctions in one of the annular rows including a cantilevered portion of the stent extending in a circumferential direction generally perpendicular to a flow direction through the prosthetic heart valve from the inflow end to the outflow end;

a cuff attached to the annulus section of the stent by cuff sutures that have a plurality of stitches extending through material of the cuff and looping around the struts and the cantilevered portions; and a plurality of leaflets each having a belly attached to the cuff within an interior region of the stent, the leaflets together having a coapted position occluding the interior region of the stent and an open position in which the interior region is not occluded, the belly of each leaflet being attached to the cuff by leaflet sutures extending in a path that crosses some of the cantilevered portions in overlap zones, wherein movement of the leaflets during the intended use of the prosthetic heart valve causes the cantilevered portions to bend in a radially inward direction at locations within the overlap zones, the radially inward direction being perpendicular to the flow direction.

2. The prosthetic heart valve as claimed in claim 1, wherein each of the junctions in the one annular row includes one of the cantilevered portions.

3. The prosthetic heart valve as claimed in claim 1, wherein each of the cantilevered portions includes a first arm connected to an end of a first strut in a cell in the one annular row and a second arm connected to an end of a second strut in the cell in the one annular row, the first arm and the second arm extending in the circumferential direction.

4. The prosthetic heart valve as claimed in claim 3, wherein an end of the first arm is connected to an end of the second arm at a joint.

5. The prosthetic heart valve as claimed in claim 3, wherein the first arm and the second arm are nonlinear.

6. The prosthetic heart valve as claimed in claim 1, wherein each of the cantilevered portions is spaced apart from the inflow end of the stent by a same distance.

7. The prosthetic heart valve as claimed in claim 1, wherein the stitches attach the cuff to the cantilevered portions within the overlap zones.

8. The prosthetic heart valve as claimed in claim 1, wherein the overlap zones are first overlap zones, some of the leaflet sutures cross a group of the struts in second overlap zones, and some of the struts in the group are devoid of the stitches within the second overlap zones.

9. The prosthetic heart valve as claimed in claim 1, wherein the leaflets are attached to the cuff by the leaflet sutures both in the overlap zones and outside of the overlap zones.

10. The prosthetic heart valve as claimed in claim 1, wherein a first group of the cantilevered portions have a first length in the circumferential direction and a second group of the cantilevered portions have a second length in the circumferential direction different from the first length.

11. The prosthetic heart valve as claimed in claim 1, wherein the path of the leaflet sutures does not cross all of the cantilevered portions.

12. The prosthetic heart valve as claimed in claim 1, wherein the path of the leaflet sutures crosses the stent only at the cantilevered portions.

13. A prosthetic heart valve, comprising:

an expandable stent having an inflow end, an outflow end, an annulus section adjacent the inflow end, a plurality of struts forming cells connected to one another in a plurality of annular rows around the stent, the cells in each of the annular rows being connected to adjacent cells in a same annular row at junctions, at least some of the cells in one of the annular rows including a cantilevered portion of the stent;

a cuff attached to the annulus section of the stent by cuff sutures that have a plurality of stitches extending through material of the cuff and looping around the struts; and a plurality of leaflets each having a belly attached to the cuff within an interior region of the stent, the leaflets together having a coapted position occluding the interior region of the stent and an open position in which the interior region is not occluded, the belly of each leaflet being attached to the cuff by leaflet sutures extending in a path that crosses some of the cantilevered portions in overlap zones, wherein movement of the leaflets during the intended use of the prosthetic heart valve causes the cantilevered portions to bend in a radially inward direction at locations within the overlap zones, the radially inward direction being perpendicular to a flow direction through the prosthetic heart valve.

14. The prosthetic heart valve as claimed in claim 13, wherein ones of the cantilevered portions extend in the flow direction.

15. The prosthetic heart valve as claimed in claim 13, wherein ones of the cantilevered portions extend in a direction transverse to the flow direction.

16. The prosthetic heart valve as claimed in claim 13, wherein the stitches attach the cuff to the cantilevered portions within the overlap zones.

17. The prosthetic heart valve as claimed in claim 13, wherein the overlap zones are first overlap zones, some of the leaflet sutures cross a group of the struts in second overlap zones, and some of the struts in the group are devoid of the stitches within the second overlap zones.

18. The prosthetic heart valve as claimed in claim 13, wherein each of the cantilevered portions includes a first arm connected to a first strut of a cell in the one annular row and a second arm connected to a second strut of the cell in the one annular row.

19. The prosthetic heart valve as claimed in claim 18, wherein the first arm is connected to the second arm.

20. The prosthetic heart valve as claimed in claim 13, wherein the one annular row is a first annular row or a second annular row at the inflow end of the stent.

* * * * *